United States Patent [19]
Avraham et al.

[11] Patent Number: 5,696,086
[45] Date of Patent: Dec. 9, 1997

[54] METHODS AND KITS USING MACROPHAGE STIMULATING PROTEIN

[75] Inventors: Hava Karsenty Avraham, Brookline, Mass.; Paul J. Godowski, Burlingame, Calif.

[73] Assignees: Genentech, Inc., South San Francisco, Calif.; Beth Israel Deaconess Medical Center, Inc., Boston, Mass.

[21] Appl. No.: 334,177

[22] Filed: Nov. 3, 1994

[51] Int. Cl.$^6$ .......................... A61K 38/16; A61K 38/19; C07K 14/00; C07K 14/52
[52] U.S. Cl. .......................... 514/12; 530/351; 530/380
[58] Field of Search ................................ 530/351, 380, 530/12; 514/2

[56] References Cited

U.S. PATENT DOCUMENTS

| | | | |
|---|---|---|---|
| 4,683,195 | 7/1987 | Mullis et al. | 435/6 |
| 5,219,991 | 6/1993 | Lenoard et al. | 530/351 |
| 5,227,158 | 7/1993 | Jardieu | 424/85.5 |
| 5,316,921 | 5/1994 | Godowski et al. | 435/69.4 |
| 5,328,837 | 7/1994 | Godowski et al. | 435/69.4 |
| 5,352,680 | 10/1994 | Portoghese et al. | 514/279 |
| 5,362,716 | 11/1994 | Kmiecik et al. | 514/12 |
| 5,547,931 | 8/1996 | Potempa | 514/2 |

FOREIGN PATENT DOCUMENTS

| | | |
|---|---|---|
| 2006964 | 7/1991 | Canada . |
| 278776 | 8/1988 | European Pat. Off. . |
| 71-01876 | 4/1995 | Japan . |
| 94/10312 | 5/1994 | WIPO . |

OTHER PUBLICATIONS

Gordon MS, Hoffmann G, "Growth Factors Affecting Human Thromobocytopoiesis: Potential AGents for the Treatment of Thromocytopenia", Blood, vol. 80, No. 2, pp. 302–307, Jul. 1992.

Hoffman Ronald, "Regulation of Megakaryocytopoiesis", Blood, vol. 74, No. 4, pp. 1196–1212, Sep. 1989.

Banu et al., "Modulation of Hematopoietic Progenitor Development by Recombinant Human FLT3 Ligand" *Blood* (abstract No. 1061) 84(10):269a (Nov. 1994).

Wang et al., "The Murine stk gene Product, a Transmembrane protein Tyrosine Kinase, is a Receptor for Macrophage–Stimulating Protein" *Proc. Natl. Acad. Sci. USA* 92(9):3933–3937 (1995).

*Remington's Pharmaceutical Sciences*, Olso et al., 16th edition, Mack Publishing Co. (1980).

"Partners & Projects" *Genetic Engineering News* (Advertisement for U.S. Application Ser. No. 07/914,630) p. 48 (Aug. 1994).

"The Polymerase Chain Reaction" *Current Protocols in Molecular Biology*, Ausubel et al., Greene Publishing Associates & Wiley Interscience, Chapter 15, vol. 2:15.0.1–15.8.8 (1991).

Asami et al., "Purification and Characterization of Hepatocyte Growth Factor from Injured Liver of Carbon Tetrachloride–Treated Rats" *J. Biochem.* 109:8–13 (1991).

Avraham et al., "Characterization of Adhesive Interactions between Human Endothelial Cells and Megakaryocytes" *J. Clin. Invest.* 91:2378–2384 (Jun. 1993).

Avraham et al., "Effects of the Stem Cell Factor, c–kit Ligand, on Human Megakaryocytic Cells" *Blood* 79(2):365–371 (Jan. 15, 1992).

Banu et al., "Tissue Sources of Murine Megakaryocyte Potentiator: Biochemical and Immunological Studies" *British Journal of Haematology* 75:313–318 (1990).

Bennett et al., "Extracellular domain–IgG fusion proteins for three human natriuretic peptide receptors. Hormone pharmacology and application to solid phase screening of synthetic peptide antisera" *Journal of Biological Chemistry* 266(34):23060–23067 (Dec. 5, 1991).

Bottaro et al., "Identification of the Hepatocyte Growth Factor Receptor as the c–met Proto–Oncogene Product" *Science* 251:802–804 (1991).

Bruno et al., "Effect of Interleukin 6 on in vitro Human Megakaryocytopoiesis: Its Interaction with Other Cytokines" *Experimental Hematology* 17:1038–1043 (1989).

Burstein et al., "Megakaryocytopoiesis in the Mouse: Response to Varying Platelet Demand" *Journal of Cellular Physiology* 109:333–341 (1981).

Burstein et al., "Thrombocytopoiesis in Normal and Sublethally Irradiated Dogs: Response to Human Interleukin–6" *Blood* 80(2):420–428 (Jul. 15, 1992).

Cachianes et al., "Epstein–Barr Virus–Derived Vectors for Transient and Stable Expression of Recombinant Proteins" *BioTechniques* 15(2):255–259 (1993).

Chan et al., "Identification of a Competitive HGP Antagonist Encoded by an Alternative Transcript" *Science* 254:1382–1385 (1991).

Collins et al., "Effect of PIXY321 on Hematologic Recovery After High–Dose Cyclophosphamide (CTX), Etoposide (VP–16) and Cisplatin (CDDP) (CEP) in Women with Breast Carcinoma" *Blood* (Abstract No. 1447) 82:366a (1993).

Cooper et al., "Amplification and Overexpression of the met Gene in Spontaneously Transformed NIH3T3 Mouse Fibroblasts" *EMBO Journal* 5(10):2623–2628 (1986).

Crawford et al., "Phase I/II Trial of Recombinant Human Interleukin–6 (rhIL–6) and Granulocyte Colony Stimulating Factor (rhG–CSF) Following Ifosphamide, Carboplatin and Etoposide (ICE) Chemotherapy in Patients with Advanced Non–small Cell Lung Carcinoma (NSCLC)" *Blood* (Abstract No. 1454) 82:367a (1993).

(List continued on next page.)

Primary Examiner—Cecilia J. Tsang
Assistant Examiner—Anish Gupta
Attorney, Agent, or Firm—Diane L. Marschang; Deirdre L. Conley

[57] ABSTRACT

The invention provides methods for stimulating megakaryocyte maturation and thrombocyte production using macrophage stimulating protein ("MSP"). In the methods, an effective amount of MSP can be administered in vivo, or alternatively, be used to stimulate maturation of megakaryocytes and produce thrombocytes in vitro. Methods for treating thrombocytopenia in a mammal with MSP are also provided. Kits and articles of manufacture which include MSP are further provided.

12 Claims, No Drawings

OTHER PUBLICATIONS de Sauvage et al., "Stimulation of megakaryocytopoiesis and thrombopoiesis by the c-Mpl ligand" *Nature* 369:533–538 (Jun. 16, 1994).

Dean et al., "The Human met Oncogene is Related to the Tyrosine Kinase Oncogenes" *Nature* 318:385–388 (Nov. 28, 1985).

Degan et al., "Characterization of the Mouse cDNA and Gene Coding for a Hepatocyte Growth Factor–like Protein: Expression during Development" *Biochemistry* 30:9781–9791 (1991).

Demetri et al., "Stimulation of Thrombopoiesis by Recombinant Human Interleukin-6 (IL-6) Pre- and Post-Chemotherapy in Previously Untreated Sarcoma Patients with Normal Hematopoiesis" *Blood* (Abstract No. 1452) 82:367a (1993).

Dexter et al., "Growth and Differentiation in the Hemopoietic System" *Ann. Rev. Cell Biol.* 3:423–441 (1987).

Ebbe et al, "Megakaryocyte Maturation Rate in Thrombocytopenic Rats" *Blood* 32(5):787–795 (Nov. 1968).

Fay et al., "Concomitant Administration of Interleukin-6 (rhIL-6) and Leucomax (rhGM-CSF) Following Autologous Bone Marrow Transplantation-A Phase I Trial" *Blood* (Abstract No. 1701) 82:431a (1993).

Gaudino et al., "Ron is a Heterodimeric Tyrosine Kinase Receptor Activated by the HGF Homologue MSP" *The EMBO Journal* 13(15):3524–3532 (1994).

Giordano et al., "Transfer of Motogenic and Invasive Response to Scatter Factor/Hepatocyte Growth Factor by Transfection of Human met Protooncogene" *Proc. Natl. Acad. Sci. USA* 90:649–653 (Jan. 1993).

Giordano et al., "Tyrosine Kinase Receptor Indistinguishable from the C-Met Protein" *Nature* 339:155–156 (May 11, 1989).

Gohda et al., "Purification and Partial Characterization of Hepatocyte Growth Factor from Plasma of a Patient with Fulminant Hepatic Failure" *J. Clin. Invest.* 81:414–419 (1988).

Gordon et al., "Growth Factors Affecting Human Thrombocytopoiesis: Potential Agents for the Treatment of Thrombocytopenia" *Blood* 80(2):302–307 (Jul. 15, 1992).

Graham et al., "Characteristics of a Human Cell Line Transformed by DNA from Human Adenovirus Type 5" *J. Gen. Virol.* 36:59–72 (1977).

Graham et al., "A New Technique for the Assay of Infectivity of Human Adenovirus 5 DNA" *Virology* 52:456–467 (1973).

Greenberg et al., "Characterization of a New Megakaryocytic Cell Line: The Dami Cell" *Blood* 72(6):1968–1977 (Dec. 1988).

Han et al., "Characterization of the DNF15S2 Locus on Human Chromosome 3: Identification of a Gene Coding for Four Kringle Domains with Homology to Hepatocyte Growth Factor" *Biochemistry* 30:9768–9780 (1991).

Harrison et al., "Hepatic Expression of Hepatocyte–Growth- -Factor-Like/Macrophage–Stimulating Protein mRNA in Fulminant Hepatic Failure" *Lancet* 344:27–28 (Jul. 2, 1994).

Hartmann et al., "A Functional Domain in the Heavy Chain of Scatter Factor/Hepatocyte Growth Factor Binds the c-Met Receptor and Induces Cell Dissociation but Not Mitogenesis" *Proc. Natl. Acad. Sci. USA* 89:11574–11578 (Dec. 1992).

Herodin et al., "Recombinant Glycosylated Human Interleukin-6 Accelerates Peripheral Blood Platelet Count Recovery in Radiation–Induced Bone Marrow Depression in Baboons" *Blood* 80(3):688–695 (Aug. 1, 1992).

Hoffman, "Regulation of Megakaryocytopoiesis" *Blood* 74(4):1196–1212 (1989).

Igawa et al., "Hepatocyte Growth Factor is a Potent Mitogen for Cultured Rabbit Renal Tubular Epithelial Cells" *Biochem. & Biophys. Res. Comm.* 174(2):831–838 (Jan. 31, 1991).

Ishibashi et al., "Effect of Recombinant Granulocyte–Macrophage Colony–Stimulating Factor on Murine Thrombocytopoiesis In Vitro and In Vivo" *Blood* 75(7):1433–1438 (Apr. 1, 1990).

Iwama et al., "Molecular Cloning of a Novel Receptor Tyrosine Kinase Gene, STK, Derived from Enriched Hematopoietic Stem Cells" *Blood* 83:3160–3169 (Jun. 1, 1994).

Kaushansky et al., "Promotion of Megakaryocyte Progenitor Expansion and Differentiantion by the c-Mpl Ligand Thrombopoietin" *Nature* 369:568–571 (Jun. 16, 1994).

Kimura et al., "Megakaryocytopoiesis in the Rat: Response to Thrombocytopenia Induced by Exchange Transfusion" *Experimental Hematology* 13:1048–1054 (1985).

Komatsu et al., "Growth and Differentiation of a Human Megakaryoblastic Cell Line, CMK" *Blood* 74(1);42–48 (Jul. 1989).

Leonard et al., "Isolation of Macrophage Stimulating Protein (MSP) From Human Serum" *Experimental Cell Research* 114:117–126 (1978).

Lindroos et al., "Hepatocyte Growth Factor (Hepatopoietin A) Rapidly Increases in Plasma before DNA Synthesis and Liver Regeneration Stimulated by Partial Hepatectomy and Carbon Tetrachloride Adminstration" *Hepatol.* 13:743–750 (1991).

Lok et al., "Cloning and Expression of Murine Thrombopoietin cDNA and Stimulation of Platelet Production In Vivo" *Nature* 369:565–568 (Jun. 16, 1994).

Lokker et al., "Generation and Characterization of a Competitive Antagonist of Human Hepatocyte Growth Factor, HGF/NK1" *Journal of Biological Chemistry* 268(23):17145–17150 (Aug. 15, 1993).

Lokker et al., "Structure–Function Analysis of Hepatotyte Growth Factor: Identification of Variants that Lack Mitogenic Activity Yet Retain High Affinity Receptor Binding" *EMBO Journal* 11(7):2503–2510 (1992).

Lotem et al, "Regulation of Megakaryocyte Development by Interleukin-6" *Blood* 74(5):1545–1551 (Oct. 1989).

Matsumoto et al., "Delection of Kringle Domains of the N–Terminal Hairpin Structure in Hepatocyte Growth Factor Results in Marked Decreases in Related Biological Activities" *Biochem. & Biophys. Res. Comm.* 181(2):691–699 (Dec. 16, 1991).

Matsumoto et al., "Hepatocyte Growth Factor is a Potent Stimulator of Human Melanocyte DNA Synthesis and Growth" *Biochem. & Biophys. Res. Comm.* 176:45–51 (1991).

Mattana et al., "Macrophage Fc Receptor Activity Modulates Mesangial Cell Proliferation and Matrix Synthesis" *American Journal of Physiology* 266:F568–F575 (1994).

Mazur et al., "Megakaryocytopoiesis and Platelet Production: a Review" *Experimental Hematology* 15:340–350 (1987).

Metcalf et al., "Actions of Leukaemia Inhibitory Factor on Megakaryocyte and Platelet Formation" *Ciba Foundation Symposium* 167:174–182 (1992).

Michalopoulos et al., "Control of Hepatocyte Replication by Two Serum Factors" *Cancer Research* 44:4414–4419 (Oct. 1984).

Miyazawa et al., "An Alternatively Processed mRNA Generated from Human Hepatocyte Growth Factor Gene" *European Journal of Biochemistry* 197:15–22 (1991).

Miyazawa et al., "Molecular Cloning and Sequence Analysis of cDNA for Human Hepatocyte Growth Factor" *Biochem. & Biophys. Res. Comm.* 163:967–973 (1989).

Montesano et al., "Identification of a Fibroblast–Derived Epithelial Morphogen as Hepatocyte Growth Factor" *Cell* 67:901–908 (1991).

Moore et al., "Clinical Implications of Positive and Negative Hematopoietic Stem Cell Regulators" *Blood* 78(1):1–19 (Jul. 1, 1991).

Mordenti et al., "Interspecies Scaling of Clearance and Volume Distribution Data for Five Therapeutic Proteins" *Pharmaceutical Research* 8(11):1351–1359 (1991).

Nakamura et al., "Molecular Cloning and Expression of Human Hepatocyte Growth Factor" *Nature* 342:440–443 (1989).

Nakamura et al., "Partial Purification and Characterization of Hepatocyte Growth Factor from Serum of Hepatectomized Rats" *Biochem. & Biophys. Res. Comm.* 122:1450–1459 (1984).

Nakamura et al., "Purification and Characterization of a Growth Factor from Rat Platelets for Mature Parenchymal Hepatocytes in Primary Cultures" *Proc. Natl. Acad. Sci. USA* 83:6489–6493 (1986).

Nakamura et al., "Purification and Subunit Structure of Hepatocyte Growth Factor from Rat Platelets" *FEBS Letters* 224:311–316 (1987).

Nakamura et al., "Reciprocal Modulation of Growth and Differentiated Functions of Mature Rat Hepatocytes in Primary Culture by Cell–Cell Contact and Cell Membranes" *Proc. Natl. Acad. Sci. USA* 80:7229–7233 (Dec. 1983).

Naldini et al., "Extracellular Proteolytic Cleavage by Urokinase is Required for Activation of Hepatocyte Growth Factor/Scatter Factor" *EMBO Journal* 11(13):4825–4833 (1992).

Naldini et al., "Hepatocyte Growth Factor (HGF) Stimulates the Tyrosine Kinase Activity of the Receptor Encoded by the Proto–Oncogene c–Met" *Oncogene* 6:501–504 (1991).

Naldini et al., "Scatter Factor and Hepatocyte Growth Factor are Indistingishable Ligands for the MET Receptor" *EMBO Journal* 10:2867–2878 (1991).

Odell et al., "Stimulation of Megakaryocytopoiesis by Acute Thrombocytopenia in Rats" *Blood* 48(5):765–775 (Nov. 1976).

Okajima et al., "Primary Structure of Rat Hepatocyte Growth Factor and Induction of Its mRNA During Liver Regeneration Following Hepatic Injury" *European Journal of Biochemistry* 193:375–381 (1990).

Oon et al., "Biochemical Characterization of an In–Vitro Murine Megakaryocyte Growth Activity: Megakaryocyte Potentiator" *Leukemia Research* 10(4):403–411 (1986).

Park et al., "Sequence of MET Protooncogene cDNA has Features Characteristic of the Tyrosine Kinase Family of Growth–Factor Receptors" *Proc. Natl. Acad. Sci. USA* 84:6379–6383 (1987).

Ronsin et al., "A Novel Putative Receptor Protein Tyrosine Kinase of the Met Family" *Oncogene* 8:1195–1202 (1993).

Rubin et al., "A Broad–Spectrum Human Lung Fibroblast–Derived Mitogen is a variant of Hepatocyte Growth Factor" *Proc. Natl. Acad. Sci. USA* 88:415–419 (1991).

Russell et al., "Partial Characterization of Hepatocyte Growth Factor From Rat Platelets" *Journal of Cellular Physiology* 119:183–192 (1984).

Saccone et al., "Regional Mapping of the Human Hepatocyte Growth Factor (HGF)–Scatter Factor Gene to Chromosome 7q21.1" *Genomics* 13:912–914 (1992).

Sakagucih et al., "Human Erythropoietin Stimulates Murine Megakaryopoiesis in Serum–free Culture" *Experimental Hematology* 15:1028–1034 (1987).

Schafer, A.I., "Thrombocytopenia and Disorders of Platelet Function" *Internal Medicine*, John J. Hutton et al. (eds.), 3rd edition, Little Brown & Co. pp. 1041–1048 (1990).

Seki et al., "Isolation and Expression of cDNA for Different Forms of Hepatocyte Growth Factor from Human Leukocyte" *Biochem. and Biophys. Res. Commun.* 172:321–327 (1990).

Shimamoto et al., "Hepatocyte Growth Factor–Like Protein is Identical to Macrophage Stimulating Protein" *FEBS Letters* 333(1):61–66 (Oct. 1993).

Simonsen et al., "Isolation and Expression of an Altered Mouse Dihydrofolate Reductase cDNA" *Proc. Natl. Acad. Sci. USA* 80:2495–2499 (1983).

Skeel et al., "Action and Target Cell Specificity of Human Macrophage–Stimulating Protein (MSP)" *J. of Immunology* 152:4618–4623 (1994).

Skeel et al., "Macrophage Stimulating Protein: Purification, Partial Amino Acid Sequence, and Cellular Activity" *Journal of Experimental Medicine* 173:1227–1234 (1991).

Sonoda et al., "Analysis in Serum–Free Culture of the Targets of Recombinant Human Hemopoietic Growth Factors: Interleukin 3 and Granulocyte/Macrophage–Colony-–Stimulating Factor are Specific for Early Developmental Stages" *Proc. Natl. Acad. Sci. USA* 85:4360–4364 (Jun. 1988).

Sparrow et al., "Haemopoietic Growth Factors Stimulating Murine Megakaryocytopoiesis: Interleukin–3 is Immunologically Distinct From Megakaryocyte–Potentiator" *Leukemia Research* 11(1):31–36 (1987).

Stoker et al., "Scatter Factor is a Fibroblast–Derived Modulator of Epithelial Cell Mobility" *Nature* 327:239–242 (1987).

Tanaka et al., "Isolation of Human Megakaryocytes by Immunomagnetic Beads" *British J. Haematology* 73:18–22 (1989).

Tashiro et al., "Deduced Primary Structure of Rat Hepatocyte Growth Factor and Expression of the mRNA in Rat Tissues" *Proc. Natl. Acad. Sci. USA* 87:3200–3204 (1990).

Urlaub et al., "Isolation of Chinese Hamster Cell Mutants Deficient in Dihydrofolate Reductase Activity" *Proc. Natl. Acad. Sci. USA* 77(7):4216–4220 (Jul. 1980).

van de Ven et al., "A Comparison of PIXY 321 (GM–CSF/IL–3 Fusion Protein) VS. GM–CSF+IL–3 in Inducing Myeloid Progenitor Proliferation (CFU–GM) in Both Isolated CD34+Cord Blood (CB) or Adult Bone Marrow (ABM)" *Experimental Hematology* (Abstract No. 152) 20:743 (1992).

Waldburger et al., "Stimulation of Megakaryocytopoiesis Following In Vivo Administration of Recombinant Murine Interleukin–12 (rmIL–12) in Naive Mice" *Experimental Hematology* (Abstract No. 479) 22(8):805 (1994).

Wang et al, "Antibodies to Macrophage Stimulating Protein (MSP): Specificity, Epitope Interactions, and Immunoassay of MSP in Human Serum" *Journal of Leukocyte Biology* 54:289–295 (Oct. 1993).

Wang et al., "Identification of the ron Gene Product as the Receptor for the Human Macrophage Stimulating Protein" *Science* 266:117–119 (Oct. 7, 1994).

Wang et al., "Macrophage–stimulating Protein Inhibits Induction of Nitric Oxide Production by Endotoxin or Cytokine–stimulated Mouse Macrophages" *Journal of Biological Chemistry* 269(19):14027–14031 (May 13, 1994).

Wang et al., "Proteolytic Activation of Single–chain Precursor Macrophage–stimulating Protein by Nerve Growth Factor–$\alpha$ and Epidermal Growth Factor–binding Protein, Members of the Kallikrein Family" *Journal of Biological Chemistry* 269(19):13806–13810 (May 13, 1994).

Wang et al., "Proteolytic Conversion of Single Chain Precursor Macrophage–stimulating Protein to a Biologically Active Heterodimer by Contact Enzymes of the Coagulation Cascade" *Journal of Biological Chemistry* 269(5):3436–3440 (Feb. 4, 1994).

Weider et al, "Evidence for the Identity of Human Scatter Factor and Human Hepatocyte Growth Factor" *Proc. Natl. Acad. Sci. USA* 88:7001–7005 (Aug. 1991).

Weidner et al., "Scatter Factor: Molecular Characteristics and Effect on the Invasiveness of Epithelial Cells" *Journal of Cell Biology* 111:2097–2108 (1990).

Williams et al. *Hematology*, 1st edition, New York, NY:McGraw-Hill, Inc. (1972).

Williams et al., "Hematopoietic Effects of a Granulocyte–Macrophage Colony–Stimulating Factor/Interleukin–3 Fusion Protein" *Cancer* (Abstract) 67:2705–2707 (May 15, 1991).

Williams et al., "Kinetic Analysis of Megakaryocyte Numbers and Ploidy Levels in Developing Colonies from Mouse Bone Marrow Cells" *Cell Tissue Kinetics* 15:483–494 (1982).

Williams et al., "Murine Megakaryocyte Colony Stimulating Factor: Its Relationship to Interleukin–3" *Leukemia Research* 9(12):1487–1496 (1985).

Williams et al., "The Origin, Development and Regulation of Megakaryocytes" *British Journal of Haematology* 52:173–180 (1982).

Williams et al., "PIXY321, But not GM–CSF Plus IL–3, Promotes Hematopoietic Reconstitution Following Lethal Irradiation" *Blood* 82:366a (1993).

Williams et al., "Two–Factor Requirement for Murine Megakaryocyte Colony Formation" *Journal of Cellular Physiology* 110:101–104 (1982).

Xu et al., "Interleukin–11: A Multifunctional Growth Factor Derived from the Hematopoietic Microenvironment" *Blood* 83(8):2023–2030 (Apr. 15, 1994).

Yoshimura et al., "Cloning, Sequencing, and Expression of Human Macrophage Stimulating Protein (MSP,MST1) Confirms MSP as a Member of the Family of Kringle Proteins and Locates the MSP Gene on Chromosome 3" *Journal of Biological Chemistry* 268(21):15461–15468 (Jul. 25, 1993).

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 2232 bases
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GAATTCCACC  ATGGGGTGGC  TCCCACTCCT  GCTGCTTCTG  ACTCAATGCT    50
TAGGGGTCCC  TGGCAGCGC   TCGCCATTGA  ATGACTTCCA  AGTGCTCCGG   100
GGCACAGAGC  TACAGCACCT  GCTACATGCG  GTGGTGCCCG  GGCCTTGGCA   150
GGAGGATGTG  GCAGATGCTG  AAGAGTGTGC  TGGTCGCTGT  GGGCCCTTAA   200
TGGACTGCCG  GGCCTTCCAC  TACAACGTGA  GCAGCCATGG  TTGCCAACTG   250
CTGCCATGGA  CTCAACACTC  GCCCACACG   AGGCTGCGGC  GTTCTGGGCG   300
CTGTGACCTC  TTCCAGAAGA  AAGACTACGT  ACGGACCTGC  ATCATGAACA   350
ATGGGGTTGG  GTACCGGGGC  ACCATGGCCA  CGACCGTGGG  TGGCCTGCCC   400
TGCCAGGCTT  GGAGCCACAA  GTTCCCGAAT  GATCACAAGT  ACACGCCCAC   450
TCTCCGGAAT  GGCCTGGAAG  AGAACTTCTG  CCGTAACCCT  GATGGCGACC   500
CCGGAGGTCC  TTGGTGCTAC  ACAACAGACC  CTGCTGTGCG  CTTCCAGAGC   550
TGCGGCATCA  AATCCTGCCG  GGAGGCCGCG  TGTGTCTGGT  GCAATGGCGA   600
GGAATACCGC  GGCGCGGTAG  ACCGCACGGA  GTCAGGGCGC  GAGTGCCAGC   650
GCTGGGATCT  TCAGCACCCG  CACCAGCACC  CCTTCGAGCC  GGGCAAGTTC   700
CTCGACCAAG  GTCTGGACGA  CAACTATTGC  CGGAATCCTG  ACGGCTCCGA   750
GCGGCCATGG  TGCTACACTA  CGGATCCGCA  GATCGAGCGA  GAGTTCTGTG   800
ACCTCCCCCG  CTGCGGGTCC  GAGGCACAGC  CCCGCCAAGA  GGCCACAACT   850
GTCAGCTGCT  TCCGCGGGAA  GGGTGAGGGC  TACCGGGGCA  CAGCCAATAC   900
CACCACTGCG  GGCGTACCTT  GCCAGCGTTG  GGACGCGCAA  ATCCCTCATC   950
AGCACCGATT  TACGCCAGAA  AAATACGCGT  GCAAAGACCT  TCGGGAGAAC  1000
TTCTGCCGGA  ACCCCGACGG  CTCAGAGGCG  CCCTGGTGCT  TCACACTGCG  1050
GCCCGGCATG  CGCGCGGCCT  TTTGCTACCA  GATCCGGCGT  TGTACAGACG  1100
ACGTGCGGCC  CCAGGACTGC  TACCACGGCG  CAGGGGAGCA  GTACCGCGGC  1150
ACGGTCAGCA  AGACCCGCAA  GGGTGTCCAG  TGCCAGCGCT  GGTCCGCTGA  1200
GACGCCGCAC  AAGCCGCAGT  TCACGTTTAC  CTCCGAACCG  CATGCACAAC  1250
TGGAGGAGAA  CTTCTGCCGG  AACCCAGATG  GGGATAGCCA  TGGGCCCTGG  1300
TGCTACACGA  TGGACCCAAG  GACCCCATTC  GACTACTGTG  CCCTGCGACG  1350
CTGCGCTGAT  GACCAGCCGC  CATCAATCCT  GGACCCCCA   GACCAGGTGC  1400
AGTTTGAGAA  GTGTGGCAAG  AGGGTGGATC  GGCTGGATCA  GCGGCGTTCC  1450
AAGCTGCGCG  TGGTTGGGGG  CCATCCGGGC  AACTCACCCT  GGACAGTCAG  1500
CTTGCGGAAT  CGGCAGGGCC  AGCATTTCTG  CGGGGGGTCT  CTAGTGAAGG  1550
```

-continued

```
AGCAGTGGAT ACTGACTGCC CGGCAGTGCT TCTCCTCCTG CCATATGCCT 1600

CTCACGGGCT ATGAGGTATG GTTGGGCACC CTGTTCCAGA ACCCACAGCA 1650

TGGAGAGCCA AGCCTACAGC GGGTCCCAGT AGCCAAGATG GTGTGTGGGC 1700

CCTCAGGCTC CCAGCTTGTC CTGCTCAAGC TGGAGAGATC TGTGACCCTG 1750

AACCAGCGCG TGGCCCTGAT CTGCCTGCCC CCTGAATGGT ATGTGGTGCC 1800

TCCAGGGACC AAGTGTGAGA TTGCAGGCTG GGGTGAGACC AAAGGTACGG 1850

GTAATGACAC AGTCCTAAAT GTGGCCTTGC TGAATGTCAT CTCCAACCAG 1900

GAGTGTAACA TCAAGCACCG AGGACGTGTG CGTGAGAGTG AGATGTGCAC 1950

TGAGGGACTG TTGGCCCCTG TGGGGGCCTG TGAGGGTGAC TACGGGGCC 2000

CACTTGCCTG CTTTACCCAC AACTGCTGGG TCCTGGAAGG AATTATAATC 2050

CCCAACCGAG TATGCGCAAG GTCCCGCTGG CCAGCTGTCT TCACGCGTGT 2100

CTCTGTGTTT GTGGACTGGA TTCACAAGGT CATGAGACTG GGTTAGGCCC 2150

AGCCTTGATG CCATATGCCT TGGGGAGGAC AAAACTTCTT GTCAGACATA 2200

AAGCCATGTT TCCTCTTTAT GCCTGTCTCG AG 2232
```

( 2 ) INFORMATION FOR SEQ ID NO:2:

( i ) SEQUENCE CHARACTERISTICS:
        ( A ) LENGTH: 711 amino acids
        ( B ) TYPE: amino acid
        ( D ) TOPOLOGY: linear ( x i ) SEQUENCE DESCRIPTION: SEQ ID NO:2:

```
Met Gly Trp Leu Pro Leu Leu Leu Leu Thr Gln Cys Leu Gly
 1               5                  10                  15

Val Pro Gly Gln Arg Ser Pro Leu Asn Asp Phe Gln Val Leu Arg
                20                  25                  30

Gly Thr Glu Leu Gln His Leu Leu His Ala Val Pro Gly Pro
                35                  40                  45

Trp Gln Glu Asp Val Ala Asp Ala Glu Glu Cys Ala Gly Arg Cys
                50                  55                  60

Gly Pro Leu Met Asp Cys Arg Ala Phe His Tyr Asn Val Ser Ser
                65                  70                  75

His Gly Cys Gln Leu Leu Pro Trp Thr Gln His Ser Pro His Thr
                80                  85                  90

Arg Leu Arg Arg Ser Gly Arg Cys Asp Leu Phe Gln Lys Lys Asp
                95                  100                 105

Tyr Val Arg Thr Cys Ile Met Asn Asn Gly Val Gly Tyr Arg Gly
                110                 115                 120

Thr Met Ala Thr Thr Val Gly Gly Leu Pro Cys Gln Ala Trp Ser
                125                 130                 135

His Lys Phe Pro Asn Asp His Lys Tyr Thr Pro Thr Leu Arg Asn
                140                 145                 150

Gly Leu Glu Glu Asn Phe Cys Arg Asn Pro Asp Gly Asp Pro Gly
                155                 160                 165

Gly Pro Trp Cys Tyr Thr Thr Asp Pro Ala Val Arg Phe Gln Ser
                170                 175                 180

Cys Gly Ile Lys Ser Cys Arg Glu Ala Ala Cys Val Trp Cys Asn
                185                 190                 195

Gly Glu Glu Tyr Arg Gly Ala Val Asp Arg Thr Glu Ser Gly Arg
                200                 205                 210
```

-continued

| | | | | | | | | | | | | | | |
|---|---|---|---|---|---|---|---|---|---|---|---|---|---|---|
| Glu | Cys | Gln | Arg | Trp 215 | Asp | Leu | Gln | His 220 | Pro | His | Gln | His | Pro | Phe 225 |
| Glu | Pro | Gly | Lys | Phe 230 | Leu | Asp | Gln | Gly 235 | Leu | Asp | Asp | Asn | Tyr | Cys 240 |
| Arg | Asn | Pro | Asp | Gly 245 | Ser | Glu | Arg | Pro 250 | Trp | Cys | Tyr | Thr | Thr | Asp 255 |
| Pro | Gln | Ile | Glu | Arg 260 | Glu | Phe | Cys | Asp 265 | Leu | Pro | Arg | Cys | Gly | Ser 270 |
| Glu | Ala | Gln | Pro | Arg 275 | Gln | Glu | Ala | Thr 280 | Thr | Val | Ser | Cys | Phe | Arg 285 |
| Gly | Lys | Gly | Glu | Gly 290 | Tyr | Arg | Gly | Thr 295 | Ala | Asn | Thr | Thr | Thr | Ala 300 |
| Gly | Val | Pro | Cys | Gln 305 | Arg | Trp | Asp | Ala 310 | Gln | Ile | Pro | His | Gln | His 315 |
| Arg | Phe | Thr | Pro | Glu 320 | Lys | Tyr | Ala | Cys 325 | Lys | Asp | Leu | Arg | Glu | Asn 330 |
| Phe | Cys | Arg | Asn | Pro 335 | Asp | Gly | Ser | Glu 340 | Ala | Pro | Trp | Cys | Phe | Thr 345 |
| Leu | Arg | Pro | Gly | Met 350 | Arg | Ala | Ala | Phe 355 | Cys | Tyr | Gln | Ile | Arg | Arg 360 |
| Cys | Thr | Asp | Asp | Val 365 | Arg | Pro | Gln | Asp 370 | Cys | Tyr | His | Gly | Ala | Gly 375 |
| Glu | Gln | Tyr | Arg | Gly 380 | Thr | Val | Ser | Lys 385 | Thr | Arg | Lys | Gly | Val | Gln 390 |
| Cys | Gln | Arg | Trp | Ser 395 | Ala | Glu | Thr | Pro 400 | His | Lys | Pro | Gln | Phe | Thr 405 |
| Phe | Thr | Ser | Glu | Pro 410 | His | Ala | Gln | Leu 415 | Glu | Glu | Asn | Phe | Cys | Arg 420 |
| Asn | Pro | Asp | Gly | Asp 425 | Ser | His | Gly | Pro 430 | Trp | Cys | Tyr | Thr | Met | Asp 435 |
| Pro | Arg | Thr | Pro | Phe 440 | Asp | Tyr | Cys | Ala 445 | Leu | Arg | Arg | Cys | Ala | Asp 450 |
| Asp | Gln | Pro | Pro | Ser 455 | Ile | Leu | Asp | Pro 460 | Pro | Asp | Gln | Val | Gln | Phe 465 |
| Glu | Lys | Cys | Gly | Lys 470 | Arg | Val | Asp | Arg 475 | Leu | Asp | Gln | Arg | Arg | Ser 480 |
| Lys | Leu | Arg | Val | Val 485 | Gly | Gly | His | Pro 490 | Gly | Asn | Ser | Pro | Trp | Thr 495 |
| Val | Ser | Leu | Arg | Asn 500 | Arg | Gln | Gly | Gln 505 | His | Phe | Cys | Gly | Gly | Ser 510 |
| Leu | Val | Lys | Glu | Gln 515 | Trp | Ile | Leu | Thr 520 | Ala | Arg | Gln | Cys | Phe | Ser 525 |
| Ser | Cys | His | Met | Pro 530 | Leu | Thr | Gly | Tyr 535 | Glu | Val | Trp | Leu | Gly | Thr 540 |
| Leu | Phe | Gln | Asn | Pro 545 | Gln | His | Gly | Glu 550 | Pro | Ser | Leu | Gln | Arg | Val 555 |
| Pro | Val | Ala | Lys | Met 560 | Val | Cys | Gly | Pro 565 | Ser | Gly | Ser | Gln | Leu | Val 570 |
| Leu | Leu | Lys | Leu | Glu 575 | Arg | Ser | Val | Thr 580 | Leu | Asn | Gln | Arg | Val | Ala 585 |
| Leu | Ile | Cys | Leu | Pro 590 | Pro | Glu | Trp | Tyr 595 | Val | Val | Pro | Pro | Gly | Thr 600 |
| Lys | Cys | Glu | Ile | Ala 605 | Gly | Trp | Gly | Glu 610 | Thr | Lys | Gly | Thr | Gly | Asn 615 |

| | | | | | | | | | | | | | | |
|---|---|---|---|---|---|---|---|---|---|---|---|---|---|---|
| Asp | Thr | Val | Leu | Asn<br>620 | Val | Ala | Leu | Leu | Asn<br>625 | Val | Ile | Ser | Asn | Gln<br>630 |
| Glu | Cys | Asn | Ile | Lys<br>635 | His | Arg | Gly | Arg | Val<br>640 | Arg | Glu | Ser | Glu | Met<br>645 |
| Cys | Thr | Glu | Gly | Leu<br>650 | Leu | Ala | Pro | Val | Gly<br>655 | Ala | Cys | Glu | Gly | Asp<br>660 |
| Tyr | Gly | Gly | Pro | Leu<br>665 | Ala | Cys | Phe | Thr | His<br>670 | Asn | Cys | Trp | Val | Leu<br>675 |
| Glu | Gly | Ile | Ile | Ile<br>680 | Pro | Asn | Arg | Val | Cys<br>685 | Ala | Arg | Ser | Arg | Trp<br>690 |
| Pro | Ala | Val | Phe | Thr<br>695 | Arg | Val | Ser | Val | Phe<br>700 | Val | Asp | Trp | Ile | His<br>705 |
| Lys | Val | Met | Arg | Leu<br>710 | Gly<br>711 | | | | | | | | | |

( 2 ) INFORMATION FOR SEQ ID NO:3:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( x i ) SEQUENCE DESCRIPTION: SEQ ID NO:3:

CAGTGCAGCC TCCAGCCAGA A 21

( 2 ) INFORMATION FOR SEQ ID NO:4:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( x i ) SEQUENCE DESCRIPTION: SEQ ID NO:4:

CTGTACAACG CCGGATCTGG TAG 23

( 2 ) INFORMATION FOR SEQ ID NO:5:

( i ) SEQUENCE CHARACTERISTICS:
        ( A ) LENGTH: 47 bases
        ( B ) TYPE: nucleic acid
        ( C ) STRANDEDNESS: single
        ( D ) TOPOLOGY: linear ( x i ) SEQUENCE DESCRIPTION: SEQ ID NO:5:

AGGACGAATC CACCATGGGG TGGCTCCCAC TCCTGCTGCT TCTGACT 47

( 2 ) INFORMATION FOR SEQ ID NO:6:

( i ) SEQUENCE CHARACTERISTICS:
        ( A ) LENGTH: 31 bases
        ( B ) TYPE: nucleic acid
        ( C ) STRANDEDNESS: single
        ( D ) TOPOLOGY: linear ( x i ) SEQUENCE DESCRIPTION: SEQ ID NO:6:

CCGGAATTCG AACTTCTGCC GGAACCCCGA C 31

( 2 ) INFORMATION FOR SEQ ID NO:7:

( i ) SEQUENCE CHARACTERISTICS:
        ( A ) LENGTH: 31 bases
        ( B ) TYPE: nucleic acid ( C ) STRANDEDNESS: single
( D ) TOPOLOGY: linear ( x i ) SEQUENCE DESCRIPTION: SEQ ID NO:7:

CCGGAATTCG AACTTCTGCC GGAACCCCGA C 31

( 2 ) INFORMATION FOR SEQ ID NO:8:

( i ) SEQUENCE CHARACTERISTICS:
( A ) LENGTH: 32 bases
( B ) TYPE: nucleic acid
( C ) STRANDEDNESS: single
( D ) TOPOLOGY: linear ( x i ) SEQUENCE DESCRIPTION: SEQ ID NO:8:

ACGGAATTCC CAAGGCATAT GGCATCAAGG CT 32

( 2 ) INFORMATION FOR SEQ ID NO:9:

( i ) SEQUENCE CHARACTERISTICS:
( A ) LENGTH: 47 bases
( B ) TYPE: nucleic acid
( C ) STRANDEDNESS: single
( D ) TOPOLOGY: linear ( x i ) SEQUENCE DESCRIPTION: SEQ ID NO:9:

GATCCGCAGA TCGAGCGAGA ATTCTGTACC TGCCGCGGTG CGAGACG 47

( 2 ) INFORMATION FOR SEQ ID NO:10:

( i ) SEQUENCE CHARACTERISTICS:
( A ) LENGTH: 49 bases
( B ) TYPE: nucleic acid
( C ) STRANDEDNESS: single
( D ) TOPOLOGY: linear ( x i ) SEQUENCE DESCRIPTION: SEQ ID NO:10:

GTGACCGTCT CGCACCGCGG CAGGTCACAG AATTCTCGCT CGATCTGCG 49

METHODS AND KITS USING MACROPHAGE STIMULATING PROTEIN

FIELD OF INVENTION

The invention relates generally to methods of stimulating megakaryocytopoiesis and thrombocytopoiesis. More particularly, the invention relates to methods of stimulating megakaryocyte maturation and thrombocyte production using macrophage stimulating protein. The invention also relates to methods of treating certain hematopoietic disorders, such as thrombocytopenia, and to kits containing macrophage stimulating protein.

BACKGROUND OF THE INVENTION

1. Hepatocyte Growth Factor

Hepatocyte growth factor ("HGF") functions as a growth factor for particular tissues and cell types. HGF was identified initially as a mitogen for hepatocytes [Michalopoulos et al., *Cancer Res.*, 44: 4414–4419 (1984); Russel et al., *J. Cell. Physiol.*, 119: 183–192 (1984); Nakamura et al., *Biochem. Biophys. Res. Comm.*, 122: 1450–459 (1984)]. Nakamura et al., supra, reported the purification of HGF from the serum of partially hepatectomized rats. Subsequently, HGF was purified from rat platelets, and its subunit structure was determined [Nakamura et al., *Proc. Natl. Acad. Sci. USA*, 83: 6489–6493 (1986); Nakamura et al., *FEBS Letters*, 224: 311–316 (1987)]. The purification of human HGF ("huHGF") from human plasma was first described by Gohda et al., *J. Clin. Invest.*, 81: 414–419 (1988).

Both rat HGF and huHGF have been molecularly cloned, including the cloning and sequencing of a naturally occurring variant lacking 5 amino acids designated "delta5 HGF" [Miyazawa et al., *Biochem. Biophys. Res. Comm.*, 163: 967–973 (1989); Nakamura et al., *Nature*, 342: 440–443 (1989); Seki et al, *Biochem. Biophys. Res. Commun.*, 172: 321–327 (1990); Tashiro et al., *Proc. Natl. Acad. Sci. USA*, 87: 3200–3204 (1990); Okajima et al., *Eur. J. Biochem.*, 193: 375–381 (1990)].

The mature form of huHGF, corresponding to the major form purified from human serum, is a disulfide linked heterodimer derived by proteolytic cleavage of the human pro-hormone between amino acids R494 and V495. This cleavage process generates a molecule composed of an α-subunit of 440 amino acids ($M_r$ 69 kDa) and a β-subunit of 234 amino acids ($M_r$ 34 kDa). The nucleotide sequence of the huHGF cDNA reveals that both the α- and the β-chains are contained in a single open reading frame coding for a pre-pro precursor protein. In the predicted primary structure of mature huHGF, an interchain S—S bridge is formed between Cys 487 of the α-chain and Cys 604 in the β-chain [see Nakamura et al., *Nature*, supra]. The N-terminus of the α-chain is preceded by 54 amino acids, starting with a methionine group. This segment includes a characteristic hydrophobic leader (signal) sequence of 31 residues and the prosequence. The α-chain starts at amino acid (aa) 55, and contains four kringle domains. The kringle 1 domain extends from about aa 128 to about aa 206, the kringle 2 domain is between about aa 211 and about aa 288, the kringle 3 domain is defined as extending from about aa 303 to about aa 383, and the kringle 4 domain extends from about aa 391 to about aa 464 of the α-chain.

The definition of the various kringle domains is based on their homology with kringle-like domains of other proteins (prothrombin, plasminogen), therefore, the above limits are only approximate. As yet, the function of these kringles has not been determined. The β-chain of huHGF shows high homology to the catalytic domain of serine proteases (38% homology to the plasminogen serine protease domain). However, two of the three residues which form the catalytic triad of serine proteases are not conserved in huHGF. Therefore, despite its serine protease-like domain, huHGF appears to have no proteolytic activity, and the precise role of the β-chain remains unknown. HGF contains four putative glycosylation sites, which are located at positions 294 and 402 of the α-chain and at positions 566 and 653 of the β-chain.

In a portion of cDNA isolated from human leukocytes, in-frame deletion of 15 base pairs was observed. Transient expression of the cDNA sequence in COS-1 cells revealed that the encoded HGF molecule (delta5 HGF) lacking 5 amino acids in the kringle 1 domain was fully functional [Seki et al., supra].

A naturally occurring huHGF variant has been identified which corresponds to an alternative spliced form of the huHGF transcript containing the coding sequences for the N-terminal finger and first two kringle domains of mature huHGF [Chan et al., *Science*, 254: 1382–1385 (1991); Miyazawa et al., *Eur. J. Biochem.*, 197: 15–22 (1991)]. This variant, designated HGF/NK2, has been proposed to be a competitive antagonist of mature huHGF.

Comparisons of the amino acid sequence of rat HGF with that of huHGF have revealed that the two sequences are highly conserved and have the same characteristic structural features. The length of the four kringle domains in rat HGF is exactly the same as in huHGF. Furthermore, the cysteine residues are located in exactly the same positions, an indication of similar three-dimensional structures [Okajima et al., supra; Tashiro et al., supra].

The HGF receptor has been identified as the product of the c-Met proto-oncogene [Bottaro et al., *Science*, 251: 802–804 (1991); Naldini et al., *Oncogene*, 6: 501–504 (1991)]. The receptor is referred to as $p190^{MET}$ and comprises a 190-kDa heterodimeric (a disulfide-linked 50-kDa α-chain and a 145-kDa β-chain) membrane-spanning tyrosine kinase protein [Park et al., *Proc. Natl. Acad. Sci. USA*, 84: 6379–6383 (1987)]. The binding activity of HGF to its receptor is conveyed by a functional domain located in the N-terminal portion of the molecule, including the first two kringles [Matsumoto et al., *Biochem. Biophys. Res. Commun.*, 181: 691–699 (1991); Hartmann et al., *Proc. Natl. Acad. Sci.*, 89: 11574–11578 (1992); Lokker et al., *EMBO J.*, 11: 2503–2510 (1992); Lokker and Godowski, *J. Biol. Chem.*, 268: 17145–117150 (1991)]. The c-Met protein becomes phosphorylated on tyrosine residues of the 145-kDa β-subunit upon HGF binding. Both the HGF and HGF receptor genes have been mapped to the long arm of chromosome 7, within the region q11.2–q21.1 [Dean et al., *Nature*, 318: 385–388 (1985); Weidner et al., *Proc. Natl. Acad. Sci. USA*, 88: 7001–7005 (1991); Saccone et al., *Genomics*, 13: 912–914 (1992)].

It has been observed that levels of HGF increase in the plasma of patients with hepatic failure [Gohda et al., supra] and in the plasma [Lindroos et al., *Hepatol.*, 13: 734–750 (1991)] or serum [Asami et al., *J. Biochem.*, 109: 8–13 (1991)] of animals with experimentally induced liver damage. The kinetics of this response are rapid, and precedes the first round of DNA synthesis during liver regeneration. HGF has also been shown to be a mitogen for certain cell types, including melanocytes, renal tubular cells, keratinocytes, certain endothelial cells and cells of epithelial origin [Matsumoto et al., *Biochem. Biophys. Res. Commun.*, 176: 45–51 (1991); Igawa et al., *Biochem. Biophys. Res.*

Commun., 174: 831–838 (1991); Hah et al., Biochem., 30: 9768–9780 (1991); Rubin et al., Proc. Natl. Acad. Sci. USA, 88: 415–419 (1991)]. HGF can also act as a "scatter factor", an activity that promotes the dissociation of epithelial and vascular endothelial cells in vitro [Stoker et al., Nature, 327: 239–242 (1987); Weidner et al., J. Cell Biol., 111: 2097–2108 (1990); Naldini et al., EMBO J., 10: 2867–2878 (1991); Giordano et al., Proc. Natl. Acad. Sci. USA, 90: 649–653 (1993)]. Moreover, HGF has recently been described as an epithelial morphogen [Montesano et al., Cell, 67: 901–908 (1991)]. Therefore, HGF has been postulated to be important in tumor invasion and in embryonic development. Chronic c-Met/HGF receptor activation has been observed in certain malignancies [Cooper et al., EMBO J., 5: 2623 (1986); Giordano et al., Nature, 339: 155 (1989)].

HGF and HGF variants are described further in U.S. Pat. Nos. 5,227,158, 5,316,921, and 5,328,837.

2. Macrophage Stimulating Protein

A protein related to HGF has recently been identified. The protein referred to as HGF-like [Hah et al., supra; Degen et al., Biochemistry, 30: 9781 (1991); Shimamoto et al., FEBS, 333: 61–66 (1993)] or macrophage stimulating protein ("MSP") [Leonard et al., U.S. Pat. No. 5,219,991; Skeel et al., J. Exp. Med., 173: 1227–1234 (1991); Leonard et al., Exp. Cell Res., 114: 117–126 (1978); Yoshimura et al., J. Biol. Chem., 268: 15461–15468 (1993)] shares with HGF the overall four kringle structure.

The cDNA coding for MSP has been identified. The protein appears to contain a similar domain structure as HGF with four kringle domains followed by a serine protease domain. MSP is a heterodimer that includes an α-chain of 53 kDa and a β-chain of 25 kDa. MSP, however, is secreted as a single chain precursor [Yoshimura et al., supra]. Like the HGF precursor [Naldini et al., EMBO J., 11: 4825–4833 (1992)], it is presently believed that maturation of MSP into a biologically active α-β heterodimer is obtained by serum-dependent proteolytic cleavage [Wang et al., J. Biol. Chem., 269: 3436–3440 (1994); Wang et al., J. Biol. Chem., 269: 14027–14031 (1994)]. Wang et al., J. Biol. Chem., 269: 13806–13810 (1994) report that certain proteases such as serum kallikrein, Factor XIIa, nerve growth factor-gamma and epidermal growth factor-binding protein cleave and activate pro-MSP to the α-β heterodimer.

MSP has been found to bind and activate a receptor comprising a heterodimeric transmembrane glycoprotein referred to as "p185$^{RON}$" or "RON" [Gaudino et al., EMBO J., 13: 3524–3532 (1994); Wang et al., Science, 266: 117 (Oct. 7, 1994)]. This glycoprotein has two chains linked by disulphide bonds: β (150 kDa) and α (35 kDa). P185$^{RON}$ is synthesized as a single chain precursor (pr170$^{RON}$), which is subsequently converted into a mature, heterodimeric form by proteolytic cleavage. Unlike the unprocessed, single-chain precursor protein, the heterodimeric form of the protein is delivered to the cell surface.

The protein sequence encoding RON was derived from a cDNA cloned from a human keratinocyte cDNA library described by Ronsin et al., Oncogene, 8: 1195–1202 (1993). The RON cDNA encodes a protein of 1,400 amino acids which shares an overall similarity to the HGF receptor structurally and has about 63% sequence identity in the catalytic domain. Both the MSP and the RON receptor genes have been mapped to chromosome 3p2.1 [Han et al., supra; Ronsin et al., supra].

The RON receptor is expressed mainly on cells of epithelial origin and in monocytes. P185$^{RON}$ also possesses intrinsic tyrosine kinase activity that is stimulated by MSP and a MSP fusion protein, MSP-NK2 [Gaudino et al., supra]. Such tyrosine kinase activity is not stimulated, however, by HGF [Id.]. This lack of cross-reactivity has been further demonstrated by the inability of MSP to bind and activate the HGF receptor, p190$^{MET}$ [Id.].

The majority of mRNA coding for MSP is expressed in the liver. It is also expressed, at lower levels, in the lung, adrenals and placenta. To date, the physiological roles of MSP in the body have not been fully understood. Serum MSP does not increase over a 24 hour period in response to intravenous lipopolysaccharide, indicating that MSP is not likely to be an acute phase protein [Wang et al., J. Leuk. Biol., 54: 289–295 (1993)]. Yoshimura et al., supra, have reported that MSP stimulates a chemotactic response to C5a in macrophages. Leonard et al., U.S. Pat. No. 5,219,991, have disclosed the use of highly purified MSP for the treatment of pathogenic infections.

3. Megakaryocyte and Thrombocyte Production

Pluripotent stem cells found primarily in the bone marrow of mammals have the potential to give rise to different types of blood cells which circulate in the peripheral blood [Dexter et al., Ann. Rev. Cell Biol., 3: 423–441 (1987)]. The pluripotent stem cells differentiate into various cell lineages through maturational stages, thereby giving rise to committed blood cell types. One cell lineage differentiated in the bone marrow is the megakaryocytic lineage.

Regulation of megakaryocytopoiesis and thrombocyte production has been reviewed by Mazur, Exp. Hemat., 15: 248 (1987) and Hoffman, Blood, 74: 1196–1212 (1989). At least three classes of megakaryocytic progenitor cells have been identified: (1) burst forming unit megakaryocytes (BFU-MK); (2) colony-forming unit megakaryocytes (CFU-MK); and light density megakaryocyte progenitor cells (LD-CFU-MK). Maturation of megakaryocytes has also been separated into stages based on standard morphologic criteria. The earliest recognizable member of the cells is the megakaryoblast. The intermediate form of the cells is referred to as the promegakaryocyte or basophilic megakaryocyte. The later form of the cells is referred to as the mature (acidophilic, granular or platelet-producing) megakaryocyte. The mature megakaryocyte extends filaments of cytoplasm into sinusoidal spaces where they detach and fragment into individual thrombocytes or "platelets" [Williams et al., Hematology, 1st Ed., McGraw-Hill, Inc., New York, N.Y. (1972)].

Megakaryocytopoiesis is believed to involve several regulatory factors [Williams et al., Br. J. Haematol., 52: 173 (1982); Williams et al., J. Cell Phys., 110: 101 (1982)]. The early stage of megakaryocytopoiesis is believed to be mitotic, involving primarily cell proliferation and colony initiation from CFU-MK but not affected by platelet count [Burstein et al., J. Cell Phys., 109: 333 (1981); Kimura et al., Exp. Hematol., 13: 1048 (1985)]. The later stage of maturation is primarily non-mitotic, involving nuclear polyploidization and cytoplasmic maturation [Odell et al., Blood, 48: 765 (1976); Ebbe et al., Blood, 32: 787 (1968)].

Thrombocytes generally circulate in the blood and play an important role in blood clotting and the body's response to injury. Decreases in the circulating levels of thrombocytes in the blood can result from various pathological conditions and therapies. Thrombocytopenia, for instance, can result from impaired production of thrombocytes by the bone marrow, thrombocyte sequestration in the spleen, and increased destruction of thrombocytes by radiation or chemical therapy. Patients receiving large volumes of rapidly administered blood products can also develop thrombocytopenia due to dilution of the blood. Thrombopoietic disorders are further described in Schafner, "Thrombocytopenia and Disorders of Platelet Function," *Internal Medicine*, 3rd Ed., Hutton et al., Eds. (1990).

Certain cytokines and growth factors have been identified as inducing thrombocyte production and megakaryocyte growth. Cytokines reported to have megakaryocyte stimulating activity (MK-CSA) include interleukin-3 (IL-3) [Williams et al., *Leukemia Res.*, 9: 1487–1491 (1985)], interleukin-6 (IL-6) [Bruno et al., *Exp. Hemat.*, 17: 1038–1043 (1989)], granulocyte-macrophage colony stimulating factor (GM-CSF) [Ishibashi et al., *Blood*, 75: 1433–1438 (1990)], interleukin-11 (IL-11) [Xu et al., *Blood*, 83: 2023–2030 (1994)], erythropoietin (Epo) [Sakaguchi et al., *Exp. Hemat.*, 15: 1023–1034 (1987)], and interleukin-12 (IL-12) [Waldburger et al., *Exp. Hemat.*, 22: 479a (1994) (suppl.)]. Other cytokines have been reported to modulate platelet development when combined with growth factors possessing established MK-CSA. These cytokines include IL-1α [Gordon et al., *Blood*, 80: 302–307 (1992)] and Leukemia Inhibitory Factor (LIF) [Metcalf et al., "Actions of leukemia inhibitory factor on megakaryocyte and platelet formation," Ciba Foundation Symposium]. The cMpl ligand has also been reported to be a stimulator of megakaryocytopoiesis and thrombopoiesis [de Sauvage et al., *Nature*, 369: 533–538 (1994); Lok et al., *Nature*, 369: 565–568 (1994); Kaushansky et al., *Nature*, 369: 568–571 (1994)]. Further, a synthetic protein reported to stimulate thrombopoiesis is PIXY 321 [van de Ven et al., *Exp. Hematol.*, 20: 743–751 (1992); Williams et al., *Blood*, 82: 366a (1993) (suppl.); Collins et al., *Blood*, 82: 366a (1993) (suppl.)]. PIXY 321 is a fusion protein composed of GM-CSF and IL-3 linked by a synthetic peptide chain [Williams, et al., *Cancer*, 67: 2705–2707 (1991)].

IL-3 is believed to principally affect the differentiation (earliest) phase of the thrombocytopoiesis process [Moore et al., *Blood*, 78: 1 (1991); Sonoda et al., *Proc. Natl. Acad. Sci. USA*, 85: 4360 (1988)]. IL-6 has been shown to induce megakaryocyte progenitor cell proliferation as well as maturation in murine and primate models, although some investigators have observed IL-6 effects only on cell maturation. The interaction between IL-3 and IL-6 is currently unclear, with some reports indicating that the MK-CSA of IL-3 is mediated by IL-6 since antibodies against murine IL-6 were found to abrogate the MK-CSA of murine IL-3 [Lotem et al., *Blood*, 74: 1545–1551 (1989)]. Other investigators have reported that neutralizing antibodies to IL-6 alone do not diminish the MK-CSA of serum prepared from aplastic patients, and hypothesize a less crucial role for IL-6 in megakaryocytopoiesis. Nevertheless, a number of studies have demonstrated a stimulatory effect of IL-6 when administered to lethally irradiated animals [Burstein et al., *Blood*, 80: 420–428 (1992); Herodin et al., *Blood*, 80: 68–74 (1992)].

In patients receiving high dose chemotherapy for metastatic sarcoma and lung cancer, IL-6 has reduced the decline in platelet count and hastened the recover to baseline levels [Demetri et al., *Blood*, 82: 367a (1993) (suppl.); Crawford et al., *Blood*, 82: 367a (1993) (suppl.)]. Autologous bone marrow transplant recipients treated with IL-6 have been reported to experience a relatively rapid return of circulating platelets and a shorter period of platelet transfusion dependence than matched controls [Fay et al., *Blood*, 82: 431a (1993) (suppl.)].

It is an object of the present invention to identify a molecule capable of stimulating production of thrombocytes in vivo and in vitro.

It is another object of the invention to identify a molecule capable of stimulating maturation of megakaryocytes in vivo and in vitro.

It is another object of the invention to provide the molecule in a pharmaceutically-acceptable carrier for use in the treatment of physiological conditions characterized by existing or anticipated low levels of circulating thrombocytes.

It is a further object of the invention to provide the molecule in an article of manufacture or kit that can be employed for purposes of stimulating production of thrombocytes and maturation of megakaryocytes.

These and other objects of the invention will be apparent to those of ordinary skill in the art upon consideration of the application as a whole.

SUMMARY OF THE INVENTION

Accordingly, in one embodiment of the invention, there is provided a method for stimulating thrombocyte production using macrophage stimulating protein.

In another embodiment of the invention, there is provided a method for stimulating megakaryocyte maturation.

In a further embodiment of the invention, there is provided an article of manufacture and kit that include macrophage stimulating protein. The macrophage stimulating protein is provided in a container having a label which identifies the macrophage stimulating protein as an active agent for stimulating megakaryocyte maturation and thrombocyte production.

Reduced levels of thrombocytes in the blood can jeopardize the health of individuals. As discussed in the Background of the Invention, dangerously low levels of thrombocytes in the blood can be the result of a variety of pathological conditions, as well as chemotherapies and irradiation. Applicants have surprisingly found that macrophage stimulating protein is useful for stimulating maturation of megakaryocytes and production of thrombocytes. The macrophage stimulating protein of the present invention can be employed in vitro and in vivo. For in vivo use, the macrophage stimulating protein can be administered as a curative therapy for those individuals suffering from hematopoietic disorders like thrombocytopenia. The macrophage stimulating protein can also be administered as a prophylactic therapy for individuals undergoing, or about to undergo, radiation and/or chemical therapies.

DETAILED DESCRIPTION OF THE PREFERRED EMBODIMENTS

1. Definitions

As used herein, the terms "macrophage stimulating protein" and "MSP" refer to a growth factor, which growth factor typically has a structure comprising four kringle domains. The terms "macrophage stimulating protein" and "MSP" refer to the mature, pre, pre-pro, and pro forms of the protein, either purified from a natural source, chemically synthesized or recombinantly produced. The macrophage stimulating protein may be in a single chain form or heterodimeric form. The present definition specifically includes macrophage stimulating protein encoded by the sequence published by Yoshimura et al., *J. Biol. Chem.*, 268: 15461–15468 (1993) (available from EMBL/GenBank/DDBJ under accession number L11924; the nucleotide and amino acid sequence also being provided herein in the SEQUENCE LISTING as SEQ ID NO:1 and SEQ ID NO:2, respectively). The fusion protein referred to herein as "MSP-NK2" comprising the N-terminal region (the first two kringle domains) of macrophage stimulating protein fused with a C-terminal region of the human IgG-gamma1 heavy chain is also specifically included in the present definition. Fragments of macrophage stimulating protein may have the same activities described herein for macrophage stimulating protein, and the use of fragments with such activity is considered to come within the scope of the present invention.

The terms "amino acid" and "amino acids" refer to all naturally occurring L-α-amino acids. This definition is meant to include norleucine, ornithine, and homocysteine. The amino acids are identified by either the single-letter or three-letter designations:

| Asp | D | aspartic acid | Ile | I | isoleucine |
|-----|---|---------------|-----|---|------------|
| Thr | T | threonine     | Leu | L | leucine    |
| Ser | S | serine        | Tyr | Y | tyrosine   |
| Glu | E | glutamic acid | Phe | F | phenylalanine |
| Pro | P | proline       | His | H | histidine  |
| Gly | G | glycine       | Lys | K | lysine     |
| Ala | A | alanine       | Arg | R | arginine   |
| Cys | C | cysteine      | Trp | W | tryptophan |
| Val | V | valine        | Gln | Q | glutamine  |
| Met | M | methionine    | Asn | N | asparagine |

The term "megakaryocyte maturation" refers to a process involving differentiation of megakaryoblasts and promegakaryocytes or basophilic megakaryocytes into mature, platelet-producing cells. Megakaryocyte maturation is typically accompanied by cellular changes, such as increased ploidy and demarcation of membranes, and can be observed and quantitated, for instance, by ploidy analysis and microscopic analysis.

The term "thrombocytopenia" refers to a physiological condition typically characterized by a thrombocyte level below about $150 \times 10^9$/liter blood.

The terms "treating," "treatment," and "therapy" refer to curative therapy, prophylactic therapy, and preventative therapy.

The term "mammal" refers to any mammal classified as a mammal, including humans, cows, horses, dogs and cats. In a preferred embodiment of the invention, the mammal is a human.

2. Methods and Compositions of the Invention

The present invention provides methods for stimulating megakaryocyte maturation and thrombocyte production using macrophage stimulating protein, referred to hereinafter as "MSP". The MSP useful in the practice of the present invention can be prepared in a number of ways. For instance, the MSP can be prepared using an isolated or purified form of MSP. Methods of isolating and purifying MSP from natural sources are known in the art and are described, for example, by Skeel et al., *J. Exp. Med.*, 173: 1227–1234 (1991) and Leonard et al., U.S. Pat. No. 5,219,991. Such isolation and purification methods can be employed for obtaining MSP from serum or plasma. Alternatively, MSP can be chemically synthesized and prepared using recombinant DNA techniques known in the art and described in further detail in Examples 1, 2 and 3 below.

The MSP may be from human or any non-human species. For instance, a mammal may have administered MSP from a different mammalian species (e.g., mice can be treated with human MSP). There is substantial homology (about 81% amino acid identity) between mouse MSP and human MSP, and thus, it is expected that MSP from different mammalian species can be employed. Preferably, however, the mammal is treated with homologous MSP (e.g., humans are treated with human MSP) to avoid potential immune reactions to the MSP.

The present invention includes methods for stimulating megakaryocyte maturation and thrombocyte production in vivo and in vitro. In accordance with the method of the invention for stimulating megakaryocyte maturation in vitro, bone marrow cells or cell samples suspected of containing megakaryoblasts, promegakaryocytes and/or basophilic megakaryocytes are provided and placed in a cell culture medium. The cells are then cultured in the presence of an effective amount of MSP.

Suitable tissue culture media are well known to persons skilled in the art and include, but are not limited to, Minimal Essential Medium ("MEM"), RPMI-1640, and Dulbecco's Modified Eagle's Medium ("DMEM"). These tissue culture medias are commercially available from Sigma Chemical Company (St. Louis, Mo.) and GIBCO (Grand Island, N.Y.). The cells are then cultured in the cell culture medium under conditions sufficient for the cells to remain viable and grow. The cells can be cultured in a variety of ways, including culturing in a clot, agar, or liquid culture.

The cells are cultured in the presence of an effective amount of MSP. The amount of MSP may vary, but preferably is in the range of about 10 ng/ml to about 100 ng/ml. The MSP can of course be added to the culture at a dose determined empirically by those in the art without undue experimentation. The concentration of MSP in the culture will depend on various factors, such as the conditions under which the cells and MSP are cultured. The specific temperature and duration of incubation, as well as other culture conditions, can be varied depending on such factors as, e.g., the concentration of the MSP, and the type of cells and medium. Those skilled in the art will be able to determine operative and optimal culture conditions without undue experimentation. Maturation of megakaryocytes in the cultures can be determined by various assays known in the art, such as those described in Williams et al., *Leukemia Res.*, 9: 1487–1491 (1985); Bruno et al., *Exp. Hematol.*, 17: 1038–1043 (1989); Ishibashi et al., *Blood*, 75: 1433–1438 (1990); Xu et al., *Blood*, 83: 2023–2030 (1994); Sakaguchi et al., *Exp. Hematol.*, 15: 1023–1034 (1987)].

It is contemplated that using MSP to stimulate megakaryocyte maturation in vitro will be useful in a variety of ways. For instance, megakaryocytes cultured in vitro in the presence of MSP can be infused into a mammal suffering from reduced levels of platelet-forming cells.

In accordance with the method of the invention for stimulating megakaryocyte maturation and thrombocyte production in a mammal, an effective amount of MSP is administered to the mammal. It is contemplated that the MSP may be administered at the time of, or after, administering to the mammal therapy, such as high-dose irradiation or chemotherapy, which can adversely affect blood thrombocyte levels. The MSP may also be administered prophylactically so as to avoid a decrease in blood thrombocyte levels.

The MSP is preferably administered to the mammal in a pharmaceutically-acceptable carrier. Suitable carriers and their formulations are described in *Remington's Pharmaceutical Sciences*, 16th ed., 1980, Mack Publishing Co., edited by Oslo et al. Compositions particularly well suited for the clinical administration of the MSP used to practice this invention include sterile aqueous solutions or sterile hydratable powders such as lyophilized protein. Typically, an appropriate amount of a pharmaceutically-acceptable salt is also used in the formulation to render the formulation isotonic. Examples of the pharmaceutically-acceptable carrier include saline, Ringer's solution and dextrose solution. It will be apparent to those persons skilled in the art that certain carriers may be more preferable depending upon, for instance, the route of administration and concentration of MSP being administered. The MSP is preferably administered to the mammal by injection (e.g., intravenous, intraperitoneal, subcutaneous, intramuscular) or by other methods such as infusion that ensure its delivery to the bloodstream in an effective form.

Effective dosages and schedules for administering MSP may be determined empirically, and making such determinations is within the skill of the art. Interspecies scaling of dosages can be performed in a manner known in the art, e.g. as disclosed in Mordenti et al., *Pharmaceut. Res.* 8: 1351 (1991). It is understood by those skilled in the art that the dose of MSP that must be administered will vary depending on, for example, the mammal which will receive the MSP, the nature of the medical condition or therapy believed to be responsible for decreased thrombocyte levels, the extent of damage to the blood cell producing tissues, the route of administration, and the identity of any other drugs being administered to the mammal. It is also understood that it may be necessary to give more than one dose of MSP. Generally, multiple doses of MSP will be required for administration. Administration of MSP should be continued until acceptable thrombocyte levels in the mammal are attained.

The invention also provides a method of treating thrombocytopenia in a mammal. In the method, the mammal is first diagnosed as suffering from thrombocytopenia. Making the diagnosis is within the skill in the art. Those skilled in the art will also appreciate that different thrombocyte levels may warrant a thrombocytopenia diagnosis for different mammalian species. The diagnosis is usually made in humans when thrombocyte levels fall below about $150 \times 10^9$ thrombocytes/liter of blood. Thrombocytopenia can be the result of a disorder of production, distribution or destruction of thrombocytes or thrombocyte-producing cells. To treat the thrombocytopenia, the MSP is administered to the mammal according to the modes and schedules of administration described above.

In the aforementioned methods, the MSP can alternatively be administered in combination with one or more biologically or chemically active agents. Preferably, such agents have megakaryocytopoietic or thrombocytopoietic activity. It is presently believed, for example, that MSP can be administered in combination with cMpl ligand or thrombopoietin [de Sauvage et al., supra; Lok et al., supra; Kaushansky et al., supra], IL-3, GM-CSF, or LIF to stimulate thrombocyte production. The skilled medical practitioner can determine the appropriate doses of each agent useful herein, generally reducing the normal dose when MSP is combined with any of these agents. The MSP can be administered in the same formulation as the other agent(s) or separate administration of MSP and the other agent(s) can occur. The other agents are administered in modes, routes, and schedules appropriate for the particular agent.

The megakaryocyte maturation and thrombocyte production can be measured or monitored in various ways. For instance, the maturation and thrombocyte production can be measured using in vitro assays. Megakaryocyte progenitor assays are known in the art and can be performed, for example, by culturing the cells in methylcellulose as described by Tanaka et al., *Br. J. Haematol*., 73: 18 (1989). Single cell growth assays can also be performed as described by Williams et al., *Cell Tissue Kinetics*, 15: 483 (1982); Banu et al., *Br. J. Haematol.*, 75: 313 (1990); Oon et al., *Leukemia Res.*, 10: 403 (1986); Sparrow et al., *Leukemia Res.*, 11: 31 (1987).

The maturation and thrombocyte production can also be monitored by peripheral blood or bone marrow analysis. Thrombocyte levels in the circulating blood can be determined by cell count analysis. The cell count analysis may be performed by counting viable cells by trypan blue exclusion. The cells can also be examined morphologically. For example, bone marrow samples can be obtained from the mammal and prepared for microscopy using standard histological techniques known in the art. By staining the cells, one can observe the size, cellular characteristics, and number of megakaryocytes in the marrow sample.

The invention further provides an article of manufacture and kit containing materials useful for stimulating megakaryocyte maturation and thrombocyte production. The article of manufacture comprises a container with a label. Suitable containers include, for example, bottles, vials, and test tubes. The containers may be formed from a variety of materials such as glass or plastic. The container holds a composition which is effective for stimulating megakaryocyte maturation and thrombocyte production. The active agent in the composition is MSP. The label on the container indicates that the composition is used for stimulating megakaryocyte maturation and thrombocyte production, and may also indicate directions for either in vivo or in vitro use, such as those described above.

The kit of the invention comprises the container described above and a second container comprising a buffer. It may further include other materials desirable from a commercial and user standpoint, including other buffers, diluents, filters, needles, syringes, and package inserts with instructions for use.

The invention will be more fully understood by reference to the following examples. They should not, however, be construed as limiting the scope of the invention. All literature citations herein are incorporated by reference.

EXAMPLES

Example 1

Recombinant Production of MSP

A cDNA encoding the full-length MSP can be constructed by joining together cDNAs encoding MSP amino acids 1–340 (clone 5' MSP) and 341–711 (clone 3' MSP) (using the numbering system reported by Yoshimura et al., supra]. These cDNAs can be isolated by PCR amplication (as described in U.S. Pat. No. 4,683,195, issued 28 Jul. 1987 and in *Current Protocols in Molecular Biology*, Ausubel et al. eds., Greene Publishing Associates and Wiley-Interscience 1991, Volume 2, Chapter 15) of cDNA from human liver. Total human liver RNA (10 ug) is used as a template for reversed transcription (RT) using a mixture of random hexamer and oligodT, using M-MLV-RT (commercially available from BRL, United Kingdom). To obtain clone 5' MSP, a PCR reaction is performed in a volume of 100 ul containing 10 ul of the RT reaction mixture, using 1 U of Vent DNA polymerase (commercially available from New England Biolabs), and 50 pmol each of the forward primer CAGTGCAGCCTCCAGCCAGAA (SEQ ID NO:3) and of the reverse primer CTGTACAACGCCGGATCTGGTAG (SEQ ID NO:4). After 30 cycles of denaturation, (95° C., 1 min.), annealing (55° C., 45 seconds), and extension (72° C., 2 min.), 2 ul of the PCR reaction is re-amplified with the nested forward primer AGGACGAATCCAC-CATGGGGTGGCTCCCACTCCTGCTGCTTCTGACT (SEQ ID NO:5) and the nested reverse primer CCGGAAT-TCGAACTTCTGCCGGAACCCCGAC (SEQ ID NO:6).

To obtain clone 3' MSP, forward primer CCGGAATTC-GAACTTCTGCCGGAACCCCGAC (SEQ ID NO:7) and reverse primer ACGGAATTCCCAAGGCATATGGCAT-CAAGGCT (SEQ ID NO:8) are used. The PCR products are digested with EcoRI restriction enzyme (commercially available from New England Biolabs), purified and cloned in the vector pRK7 (EP 278,776, published Aug. 17, 1988). The sequence of inserts amplified from separate PCR reactions can then be determined by dideoxynucleotide sequencing. The cDNA can be expressed and purified using techniques described by Yoshimura et al., supra.

Example 2

Recombinant Production of MSP/NK2 Fusion Protein

A partial cDNA containing the N-terminal 268 amino acids of MSP [using the numbering system reported by Yoshimura et al., supra] is fused to a sequence of the human IgG-gamma1 heavy chain [Bennett et al., *J. Biol. Chem.*, 266: 23060–23067 (1991)]. This can be accomplished using synthesized complementary oligonucleotide GATCCGCA-GATCGAGCGAGAATTCTGTACCTGC-CGCGGTGCGAGACG (SEQ ID NO:9) and GTGAC-CGTCTCGCACCGCGGCAGGTCACAGAATTCTCGC-TCGATCTGCG (SEQ ID NO:10) to link the MSP sequences through the unique BamHI site in MSP to the BstEII site in human IgG-gamma heavy chain cDNA [Id.]. The resulting construct contains the coding sequences of amino acids 1–268 of MSP, linker sequences encoding amino acids Glu, Thr, Val, and Thr, followed by the coding sequences of amino acids 216–443 of human IgG-gamma1 heavy chain.

The cDNA encoding MSP/NK2 can be inserted into the EBV-based expression plasmid pCIS.EBON [U.S. Pat. No. 5,328,837], and inserted into 293 cells [human embryonic kidney cell line, Graham et al., *J. Gen. Virol.*, 36: 59 (1977)] using the procedure described by Cachianes et al., *Biotechniques*, 15: 255–259 (1993). For MSP/NK2 purification, serum-free conditioned media from 293 cells expressing MSP/NK2 is sterile-filtered, and citrate buffer (pH 6) is added to give a final concentration of 100 mM citrate. All purification procedures are performed at 4° C.

The filtered media is then loaded onto a HiTrap™ Protein A column (Pharmacia LKB, Piscataway, N.J.) equilibrated with 100 mM citrate, pH 6. Bound protein is eluted in 100 mM citrate, pH 6, 3.5M $MgCl_2$, 2% (v/v) glycerol. Each fraction is immediately buffer-exchanged by passage through a PD-10 column (Sephadex G-25) preequilibrated with phosphate-buffered saline. The fraction is then pooled and concentrated. Protein concentration can be determined by an anti-human Fc ELISA (see, for example, U.S. Pat. Nos. 5,316,921 and 5,328,837) and by total amino acid hydrolysis. The NH2-terminal sequence of the purified MSP/NK2 can be confirmed by protein sequencing. Protein purity and integrity can be assessed by silver staining of SDS-PAGE gels as well as by western blotting using an antibody directed against the human Fc region of IgG1.

Example 3

Effect of MSP on Maturation of Human Megakaryocytic Cell lines

Human megakaryocytic cell lines were analyzed in vitro for their response to various concentrations of conditioned medium containing MSP and recombinant huHGF, prepared as described in sections A and B, respectively, below.

A. Preparation of Conditioned Medium Containing MSP cDNAs encoding MSP were prepared as described in Example 1. The sequence of the MSP was identical to the sequence of human MSP as reported by Yoshimura et al., supra. The cDNAs were inserted into the expression plasmid pCIS.EBON (identified in Example 2), and stable populations of 293 cells (identified in Example 2) containing these plasmids were established as described by Cachianes et al., *Biotechniques*, supra. Media from 293 control cells and MSP transfectants were treated prior to use with 5% FCS for 1 hour at 37° C. in order to allow pro-MSP processing to the mature two-chain form [Wang et al., *J. Biol. Chem.*, 269: 3436–3440 (1994)]. Conditioned medium from cells transfected either with the vector alone or with the vector containing the MSP were collected over 48 hours and were utilized at a 1:10 dilution in the assays described below.

B. Preparation of Recombinant huHGF

Recombinant huHGF was prepared essentially as described in U.S. Pat. No. 5,227,158. A huHGF cDNA clone (HLC3) isolated from a human leukocyte library as described by Seki et al., supra, was cloned into the expression vector, pSVI6B5 (ATCC Deposit No. 68,151). The complete amino acid sequence of human leukocyte HGF is shown in U.S. Pat. No. 5,227,158, SEQ ID NO:2.

CHO-dhfr⁻ cells [Urlaub et al., *Proc. Natl. Acad. Sci. USA*, 77: 4216–4220 (1980)] were cotransfected with the above-described pSVI6B5-based hHGF expression vector and with a dhfr selection vector, pFD11 [Simonsen et al., *Proc. Natl. Acad. Sci. USA*, 80: 2495–2499 (1983)], using the general procedure of Graham et al., *Virology*, 52: 456–467 (1973). The latter plasmid encodes DHFR, thereby conferring methotrexate resistance on the transfected cells and allowing for selection of huHGF expressing transformants. The transformed dhfr⁻ cells were selected by growth in glycine-, hypoxanthine- and thymidine-deficient medium. Colonies that arose on this selection medium were isolated using cotton swabs and propagated in the same medium to several generations. After cell growth, the cells were amplified and selected with increasing amounts of methotrexate using standard techniques. Clones that could grow in selective media, and therefore incorporated the transfected DHFR containing plasmid, were screened for the presence of secreted HGF. HGF activity in the media of these clones was assayed with a mitogenic assay described in Nakamura et al., *Proc. Natl. Acad. Sci. USA*, 80: 7229–7233 (1983). HGF activity in culture media may also be measured by incorporation of $^{125}$I-labelled deoxyuridine into rat hepatocytes in primary culture as described by Nakamura et al., *Nature*, 342: 440–443 (1989). The huHGF was then purified essentially as described by Nakamura et al., *Proc. Natl. Acad. Sci.*, supra.

C. Cell Culture Assays

The human megakaryocytic cell lines "DAMI" (obtained from S. Greenberg, Brigham and Women's Hospital, Boston, Mass.) and "CMK" (obtained from T. Sato, Chiba University, Japan) were employed in the assays. Both cell lines were maintained in culture as described by Greenberg et al., *Blood*, 72: 1968–174 (1988) and Komatsu et al., *Blood*, 74: 42 (1989).

Cells were plated in 24 well culture plates (Corning, Corning, N.Y.) at $2 \times 10^5$ cells/ml in RPMI-1640 medium containing 5% platelet poor plasma ("PPP") (prepared as described in Avraham et al., *Blood*, 79: 365–371 (1992)) for 5 days at 5% $CO_2$ humidified atmosphere. The cells were cultured with the MSP conditioned medium (described in Section A above), recombinant huHGF (described in Section B above) at three different concentrations or 293 cell control conditioned medium and with or without phorbol-12-myristate-13-acetate ("PMA"). The PMA was used as a positive control. The PMA was prepared by dissolving PMA (Sigma, St. Louis, Mo.) in dimethylsulfoxide (DMSO) and stored at −80° C. Just before use, the PMA was diluted in RPMI-1640 culture medium. The diluted PMA was then incubated with the cells at a concentration of 10 ng/ml. After incubation, the cells were washed twice with Hank's Balanced Salt Solution ("HBSS") and resuspended in Nuclei Isolation Medium ("NIM"; 0.2% BSA, Nonidet p40, and 10 mM EEPES pH 7.4 in HBSS) plus 54 Worthington units/ml RNase A (Biolab, New England, MA) at $2 \times 10^6$ cells/ml.

DNA content, or ploidy, of the cultured cells was examined by staining the cells with an equal volume of NIM (described above) containing 25 ug/ml propidium iodide (Sigma, St. Louis, Mo.). The samples were then kept in the dark at 4° C. and analyzed the same day using a fluorescein activated cell sorting scan (Becton Dickinson, Mountain View, Calif.) and CellFit™ software. The results are shown below in Table 1. The results are expressed as the mean±SEM of data obtained from three experiments performed in duplicate.

TABLE 1

Effect of HGF and MSP on ploidy of CMK cells

| Treatment | 2N | S-phase | 4N | >8N |
|---|---|---|---|---|
| Control | 52.2 | 28.8 | 12.9 | 3.8 |
| PMA (5 ng/ml) | 52.2 | 18.4 | 17.3 | 3.8 |
| HGF: | | | | |
| (10 ng/ml) | 60.0 | 18.4 | 13.5 | 4.3 |
| (50 ng/ml) | 57.6 | 18.4 | 12.3 | 2.7 |
| (100 ng/ml) | 59.3 | 24.7 | 11.0 | 3.38 |
| MSP 1:10 | 55.0 | 20.2 | 15.6 | 6.9 |
| Control Conditioned Medium 1:10 | 58.3 | 16.5 | 13.0 | 2.86 |

The results of the experiments revealed that MSP treatment over a range of concentrations enhanced the maturation of CMK cells as assayed by ploidy. In contrast, the huHGF over a range of concentrations had no effect on CMK ploidy.

D. Northern Blot Analysis of DAMI and CMK Cells

Total cellular RNA was extracted from the CMK and DAMI cells by a guanidine-isothiocyanate method, and 20 ug RNA was electrophoresed in 1% agarose gel with 2.2 mol/L formaldehyde. After transfer to nylon filters (Hybond-N), the filters were hybridized with labeled radioactive complementary DNA inserts. This hybridization was done at 37° C. in the presence of 50% formamide, 3× sodium chloride and sodium citrate (SSC), 0.5% sodium dodecyl sulfate (SDS), 10% dextran sulfate, and 100 ug/ml denatured salmon sperm DNA. Filters were washed at 60° C. for 2 hours in 0.2× SSC and 0.5% SDS. Membranes were then exposed to Kodak Xomat films (Eastman Kodak, Rochester, N.Y.) for 48 hours. The specific messenger RNA (mRNA) transcripts were detected with the partial human cDNA probe for RON, consisting of the kinase domain. The results of the blot analysis showed that specific transcripts of 5.0 kb and 2.0 kb of the RON gene were constitutively expressed in the CMK and DAMI cells (data not shown).

Example 4

Effect of MSP on Cytokine Secretion By Human Marrow Megakaryocytes

A. In vitro Assays

Using specific cytokine assays, supernatants from cultured human megakaryocytes and DAMI cells, treated with MSP conditioned medium or recombinant huHGF, were assayed to examine synthesis and secretion of IL-6, IL-1β and GM-CSF.

Bone marrow was aspirated from healthy donors under sterile conditions in preservative-free heparin using standard techniques. Primary bone marrow megakaryocytes were isolated by immunomagnetic beads coated with a cocktail of monoclonal antibodies to surface GpIIb/IIIa (M753, Dako, Carpenteria, Calif.), as described in Tanaka et al., *Brit. J. Haematol.*, 73: 18–24 (1989). Purity of the isolated marrow megakaryocytes was then measured by flow cytometry (using the method of Tanaka et al., supra) and determined to be 95-98%.

Isolated primary marrow megakaryocytes ($10^5$ cells/ml) and DAMI cells ($10^6$ cells/ml) (obtained from S. Greenberg, Brigham & Women's Hospital, Boston, Mass.) were cultured in RPMI-1640 medium containing 1% PPP (identified in Example 3, Section C) in the presence or absence of MSP conditioned medium (prepared as described in Example 3, Section A), recombinant huHGF (prepared as described in Example 3, Section B), or 293 cell control conditioned medium for 24 hours under conditions described by Avraham et al., supra. Duplicate cultures were maintained for each test culture. Platelet poor plasma was employed in the assays to avoid the presence of TGF-β and other platelet-derived mediators that may be present in relatively high quantities in serum.

Supernatants from the cell cultures were obtained and assayed for immunoreactive cytokines. Immunoassays for human interleukin-1β, human GM-CSF, and human interleukin-6 were purchased from R & D Systems, Minneapolis, Minn. and used according to manufacturer's instructions. A standard curve with a cytokine-positive control was run in each assay. The lower limit of detection was determined to be 0.35 pg/ml for IL-6, 1.5 pg/ml for GM-CSF, and 0.3 pg/ml for IL-1β.

The assay results, reported in Table 2 below, are expressed as the mean±SEM of data obtained from three assays performed in duplicate. Statistical significance was determined using the Student's T-test.

TABLE 2

EFFECT OF MSP AND HGF ON CYTOKINE SECRETION BY PRIMARY BONE MARROW MEGAKARYOCYTES AND DAMI CELLS

| TREATMENT | IL-6 | GM-CSF | IL-1β |
|---|---|---|---|
| Primary Marrow Megakaryocyte | 45.3 ± 4.6 | 13.0 ± 1.3 | 362.4 ± 21.5 |
| Medium + 2% PPP | | | |
| MSP | 138.9 ± 13.0* | 21.0 ± 2.0 | 412.0 ± 31.0 |
| Control Conditioned Medium | 37.3 ± 3.7 | 10.0 ± 1.0 | 361.1 ± 30.5 |
| DAMI: | 34.2 ± 3.1 | 0.8 ± 0.1 | 3.5 ± 0.5 |
| Control Conditioned Medium | | | |
| MSP | 90.2 ± 9.0* | 1.7 ± 0.3 | 4.4 ± 1.0 |

*Statistically significant compared to control conditioned medium.

As shown in Table 2, the addition of MSP elicited an increase in IL-6 secretion in all cultures examined over all other treatments. A similar increase was observed with DAMI cells; about 34 pg/ml IL-6 was detected in cultures of untreated cultures as compared to 90 pg/ml of IL-6 detected in MSP treated cultures. To a lesser extent, MSP treatment enhanced secretion of GM-CSF and IL-1β over all other treatments for primary bone marrow megakaryocytes and over the control for DAMI cells.

Secretion of IL-1β by the human megakaryocytes was also evaluated using a specific IL-1β ELISA. IL-1β protein was detected in the supernatants of unstimulated megakaryocytes. MSP modestly stimulated secretion of IL-1β but did not appear to be significant. No effect on secretion of GM-CSF by MSP or huHGF was observed.

B. RNA Analysis of Megakaryocytes

Total cellular RNA was extracted from the isolated primary bone marrow megakaryocytes. The RNA was extracted by the guanidine-isothiocyanate procedure, followed by ultra-centrifugation through a CsCl cushion. Total RNA was then run on a 1.2% formaldehyde agarose gel, and the intact RNA was visualized by ethidium bromide staining. Reversed transcription (RT) of RNA was performed using 2 ug of total RNA from each sample. PCR assays, using RON primers, were performed with forward and reverse primers.

The PCR products were analyzed on a 2% agarose gel (BRL, Bethesda, Md.). The amplified DNA bands were visualized with a UV transilluminator. Amplified DNA could be detected at the expected size by ethidium bromide staining of the gel. Internal reaction standards for PCR controls were performed. These standards included RNA with and without primers, primers without RNA, and RNA with actin primers. All the primer stocks and total preparation RNAs were analyzed to exclude contamination by cellular DNA. The results of the RNA analysis showed that the isolated bone marrow megakaryocytes expressed specific mRNAs for RON (data not shown).

Example 5

Effect of MSP on Murine Megakaryocytopoiesis

To examine the effect of MSP on murine megakaryocyte differentiation, single cell megakaryocyte growth assays were performed in accordance with the methods described in Oon et al., *Leukemia Research*, 10: 403–412 (1986) and Sparrow et al., *Leukemia Research*, 11: 31–36 (1987).

Single cell populations from bone marrow were prepared from femurs of normal C57B1/6 mice (purchased from Jackson Laboratories) by flushing the bones with DMEM containing 10% FCS. The immature megakaryocyte populations were obtained in 1.07–1.085 g/cm$^{-3}$ fractions from a suspension of single bone marrow cells separated by Percoll (Pharmacia) gradient. The fractionated cells were cultured at $10^5$ cells/ml in DMEM-10% FCS for 5 days at 37° C. in a humidified incubator of 10% $CO_2$ in the presence of titrated doses of MSP conditioned medium (prepared as described in Example 3, Section A) and IL-6 (purchased from R & D Systems, Minneapolis, Minn.).

The cultures were dried and stained for acetylcholinesterase as described by Williams et al., *Cell Tissue Kinetics*, 15: 483–494 (1982); Banu et al., *British J. Haemat.*, 75: 313–318 (1990); Oon et al., supra; Sparrow et al., supra. Single murine megakaryocytes were scored as the number of acetylcholinesterase positive cells per fractionated $5\times10^4$ bone marrow cell cultures. Immature megakaryocyte growth was quantitated by the number of single large megakaryocytes that were detected by light microscopy.

The results are shown in Table 3. The results reported are the mean±SEM from triplicate cultures from three experiments.

TABLE 3

Effect of MSP on immature murine megakaryocytes

| Treatment of Culture | Single Megakaryocytes per $5 \times 10^4$ cells |
|---|---|
| Control (FCS) | 5.6 ± 0.8 |
| IL-6 (25 ng/ml) | 13.0 ± 2.0 |
| IL-6 (25 ng/ml) + Anti-IL-6 Ab (1:10) | 5.8 ± 2.5 |
| IL-6 (25 ng/ml) + Non immune serum | 13.5 ± 1.0 |
| MSP | 14.0 ± 2.8 |
| MSP + Anti-IL-6 Ab (1:10) | 5.5 ± 0.8 |
| MSP + Non immune serum | 13.5 ± 1.5 |
| Control Conditioned Medium | 5.5 ± 1.0 |
| Control conditioned Medium + Anti-IL-6 (1:10) | 6.2 ± 1.0 |
| Control Conditioned Medium + Non immune serum | 4.8 ± 1.0 |

Addition of MSP to cultures of murine immature megakaryocyte populations showed an enhanced growth response with an increase in detectable numbers of acetylcholinesterase-positive megakaryocytes.

Neutralization assays were also conducted using an indirect immune complex depletion method [Sparrow et al., supra]. Neutralizing monoclonal antibodies for IL-6 were obtained from Genetics Institute, Boston, Mass. Suboptimal levels of growth factors (MSP and huHGF) and optimal levels of antibodies (1:10 dilution) were selected to provide an antibody excess. The various growth factors and antibodies were mixed and incubated at 4° C. for 2 hours. For controls, normal rabbit serum (purchased from Sigma, St. Louis, Mo.) was used. Immune complexes were precipitated by adding 50 ul Protein A-sepharose CL-4™ (Pharmacia LKB, Piscataway, N.J.). Culture supernatants were collected and assayed for residual megakaryocyte stimulatory activity in the immature murine megakaryocyte growth assay described above.

Results of the neutralization assays showed that the increased growth of immature murine megakaryocytes in response to MSP (as well as IL-6) was neutralized by a monoclonal antibody directed against IL-6. See Table 3. Table 3 also shows that non immune serum added to IL-6 or MSP had no significant effect over IL-6 or MSP alone. Although not fully understood and without being limited to any one theory, the results suggest that MSP may function in regulating megakaryocyte maturation by inducing cytokine secretion from the megakaryocyte or induction of IL-6 by accessory cells.

What is claimed is:

1. A method of stimulating thrombocyte production in a mammal comprising administering to the mammal an effective amount of macrophage stimulating protein.

2. The method of claim 1 wherein the macrophage stimulating protein is human macrophage stimulating protein.

3. The method of claim 1 wherein the macrophage stimulating protein is administered after chemotherapy is administered to the mammal.

4. The method of claim 1 wherein the macrophage stimulating protein is administered before chemotherapy is administered to the mammal.

5. The method of claim 1 wherein the effective amount of macrophage stimulating protein is in a sterile saline carrier.

6. A method of treating thrombocytopenia in a mammal, comprising administering to a mammal diagnosed as having thrombocytopenia an effective amount of macrophage stimulating protein.

7. A method for stimulating megakaryocyte maturation in vitro, comprising culturing a cell sample suspected of containing megakaryoblasts, promegakaryocytes and/or basophilic megakaryocytes in the presence of an effective amount of macrophage stimulating protein.

8. The method of claim 7 wherein the amount of macrophage stimulating protein is about 10 ng/ml to about 100 ng/ml.

9. An article of manufacture, comprising:
a container;
a label on said container; and
a composition contained within said container;
wherein the composition is effective for stimulating megakaryocyte maturation and thrombocyte production, the label on said container indicates that the composition can be used for stimulating megakaryocyte maturation and thrombocyte production, and the active agent in said composition comprises macrophage stimulating protein.

10. The article of manufacture of claim 9 further comprising instructions for administering the macrophage stimulating protein to a mammal.

11. The article of manufacture of claim 9 further comprising instructions for using the macrophage stimulating protein in an in vitro cell culture.

12. A kit, comprising:
a first container, a label on said container, and a composition contained within said container; wherein the composition is effective for stimulating megakaryocyte maturation and thrombocyte production, the label on said container indicates that the composition can be used for stimulating megakaryocyte maturation and thrombocyte production, and the active agent in said composition comprises macrophage stimulating protein; and
a second container comprising a buffer.

* * * * *